United States Patent
Knobloch et al.

(10) Patent No.: US 12,098,958 B2
(45) Date of Patent: Sep. 24, 2024

(54) THERMAL MEASUREMENT SYSTEM

(71) Applicant: Unison Industries, LLC, Jacksonville, FL (US)

(72) Inventors: Aaron Jay Knobloch, Niskayuna, NY (US); Christian M. Heller, Albany, NY (US)

(73) Assignee: Unison Industries, LLC, Jacksonville, FL (US)

( * ) Notice: Subject to any disclaimer, the term of this patent is extended or adjusted under 35 U.S.C. 154(b) by 766 days.

(21) Appl. No.: 17/150,003

(22) Filed: Jan. 15, 2021

(65) Prior Publication Data

US 2022/0228923 A1 Jul. 21, 2022

(51) Int. Cl.
| | |
|---|---|
| *G01J 5/58* | (2022.01) |
| *G01J 5/0802* | (2022.01) |
| *G01L 11/02* | (2006.01) |
| *G01N 21/3504* | (2014.01) |
| *G01N 33/00* | (2006.01) |

(52) U.S. Cl.
CPC ............. *G01J 5/58* (2013.01); *G01J 5/0802* (2022.01); *G01L 11/02* (2013.01); *G01N 21/3504* (2013.01); *G01N 33/0027* (2013.01)

(58) Field of Classification Search
CPC ........... G01J 5/58; G01J 5/0802; G01L 11/02; G01N 21/3504; G01N 33/0027
See application file for complete search history.

(56) References Cited

U.S. PATENT DOCUMENTS

| | | |
|---|---|---|
| 5,186,146 A | 2/1993 | Sohma et al. |
| 5,225,883 A | 7/1993 | Carter et al. |
| 6,265,712 B1 | 7/2001 | Charlier et al. |
| 7,619,742 B2 | 11/2009 | Sanders |
| 8,702,302 B2 | 4/2014 | Badami et al. |
| 8,790,006 B2 | 7/2014 | Li et al. |
| 9,335,215 B2 | 5/2016 | Wang et al. |
| 10,088,370 B2 | 10/2018 | Chrystie et al. |
| 10,697,317 B2 | 6/2020 | Bailey et al. |
| 2009/0248350 A1 | 10/2009 | Yamakage et al. |
| 2010/0063748 A1* | 3/2010 | Mottier .............. G01N 21/3504 702/24 |
| 2011/0128989 A1* | 6/2011 | Li ........................ G01J 5/0846 374/131 |
| 2023/0243704 A1* | 8/2023 | Knobloch ............. G01J 5/0806 374/121 |

FOREIGN PATENT DOCUMENTS

| | | | |
|---|---|---|---|
| EP | 0173548 B1 | 7/1991 | |
| FR | 2962215 A1 * | 1/2012 | ........... F01D 17/085 |
| WO | 2000054012 A1 | 9/2000 | |

* cited by examiner

*Primary Examiner* — Mirellys Jagan
(74) *Attorney, Agent, or Firm* — McGarry Bair PC

(57) ABSTRACT

An apparatus and method for determining a temperature in a system having an object, an optical sensor, and a gas flow passing between the object and the optical sensor, sensing, with the optical sensor, a wavelength emitted from the object and indicative of an attenuation, sensing, with the optical sensor, a wavelength emitted from the object and indicative of a temperature of at least one of the object or the gas; and calculating a temperature of the gas using the wavelengths.

16 Claims, 6 Drawing Sheets

THERMAL MEASUREMENT SYSTEM

TECHNICAL FIELD

This disclosure generally relates to thermal measurement systems, and more particularly to a multiwavelength thermometer.

BACKGROUND

Temperature measurements are performed in a wide variety of environments, including in industrial, scientific, and commercial processes. One technique utilizes a pyrometer, also referred to as an infrared thermometer, for object temperature estimation. For example, multiwavelength pyrometry can include sampling and combining radiation emitted by the object at multiple wavelengths. Other techniques utilize optical spectroscopy for measurement of gas temperatures or concentrations.

BRIEF DESCRIPTION

Aspects and advantages of the disclosure will be set forth in part in the following description, or may be obvious from the description, or may be learned through practice of the disclosure.

In one aspect, the present disclosure relates to a method of determining a temperature in a system having an object, an optical sensor, and a gas flow passing between the object and the optical sensor, the method comprising sensing, with the optical sensor, an attenuation wavelength emitted from the object and indicative of an attenuation associated with the optical sensor; sensing, with the optical sensor, at least one temperature wavelength emitted from the object and indicative of a temperature of at least one of the object or the gas; and calculating a temperature of the gas using the at least one temperature wavelength and the attenuation wavelength.

In another aspect, the present disclosure relates to a method of determining a temperature of a gas, the method comprising flowing a gas between an object and a thermal measurement system, the thermal measurement system comprising at least an optical sensor and a processor; filtering, with the optical sensor, light waves emitted from a surface of the object and having various wavelengths; sensing, with the optical sensor a gas wavelength associated with a high gas absorption and an attenuation wavelength indicative of an attenuation of the optical sensor; calculating, with the processor, a first gas temperature using the gas wavelength; determining a temperature of the object; retrieving, from a database provided in the processor, at least one parameter indicative of a gas absorption and associated with the object temperature and the first gas temperature; determining the gas absorption; calculating, with the processor, the attenuation of the optical sensor using the attenuation wavelength; and calculating an actual gas temperature with the attenuation and the gas absorption.

In another aspect, the present disclosure relates to a thermal measurement system for determining the temperature of a gas disposed around an object, the thermal measurement system comprising an optical sensor spaced from the object a predetermined distance, the optical sensor comprising an attenuation filter associated with an attenuation of the optical sensor determined by an attenuation wavelength reaching the object having passed through the gas; an optical detector for translating the attenuation wavelength into a transmitted signal; and a processor configured to receive the transmitted signal, the processor comprising a storage for storing a set of parameters and a computer for determining at least one parameter from the set of parameters associated with the transmitted signal and calculating a gas temperature of the gas utilizing the transmitted signal and the at least one parameter.

These and other features, aspects and advantages of the present disclosure will become better understood with reference to the following description and appended claims. The accompanying drawings, which are incorporated in and constitute a part of this specification, illustrate aspects of the disclosure and, together with the description, serve to explain the principles of the disclosure.

BRIEF DESCRIPTION OF THE DRAWINGS

A full and enabling disclosure of the present disclosure, including the best mode thereof, directed to one of ordinary skill in the art, is set forth in the specification, which refers to the appended figures, in which.

DETAILED DESCRIPTION

Figure 1:
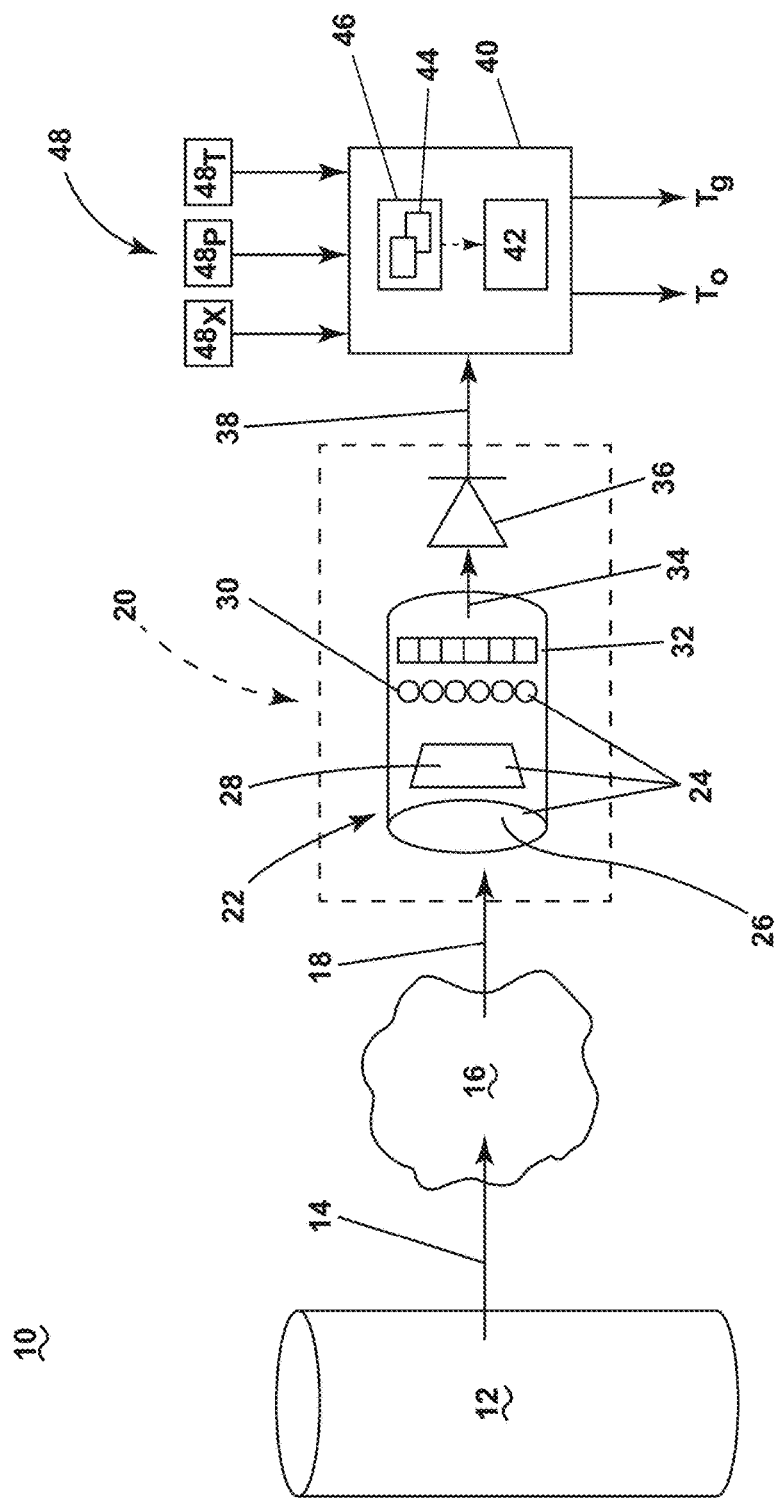
FIG. 1 is a schematic of a thermal measurement system spaced from an object and having an optical sensor.

Aspects of the disclosure described herein are directed to a thermal measurement system and method of determining the temperature of a gas. More specifically, the disclosure generally relates to the use of attenuation to more accurately determine the temperature of a gas disposed around an object, by way of non-limiting example a turbine blade. For purposes of illustration, the present disclosure will be described with respect to determining the temperature of a gas around a turbine blade for an aircraft gas turbine engine. It will be understood that aspects of the disclosure described herein are not so limited and can have general applicability within an engine, including compressors, as well as in non-aircraft applications, such as other mobile applications and non-mobile industrial, commercial, and residential applications.

Aspects of the thermal measurement system described herein can be implemented in a turbine engine. For example, as a product offering, a standalone product, a service offering, and/or a component of a service offering. Aspects of the disclosure can even be remote from the actual gas and object. For example, a computer system that employs aspects of the disclosure can be in a remote location, on stored remotely, and/or available via the Internet.

In aviation applications, and particularly in gas or combustion turbine engines where a flow of combusted gases passes through the engine onto a multitude of rotating turbine blades, monitoring the temperature of components within the turbine engine as well as the combusted gases passing through the engine is necessary for maintenance and optimal performance of the turbine engine. A thermocouple located in the exhaust can be used to measure the temperature of the exhaust gas and then modeling can occur in order to estimate component temperatures upstream. Thermocouples can become limited in reliability as combustion temperatures increase. Likewise, pyrometers, can be used to measure the temperature of component directly and then the exhaust gas temperature can be estimated based on the component temperature when the component is rotating through the exhaust gas. Pyrometry techniques can also become limited in reliability in terms of accuracy with environmental changes.

Additionally, a complicating factor for measuring temperatures in certain harsh environments is that in certain combustion regions (e.g., aircraft engines) adding devices of any sort in the combustion region is highly regulated. Therefore, there is an ongoing need for improvements in temperature measurement.

Typical multiwavelength pyrometers in combination with modeling have traditionally been used to estimate the temperature of a gas within a cooled turbine engine component. For example, an engine component with integrated cooling can have an object temperature that is a function of both the temperature of the combustion products, referred to herein as the gas temperature, but also a function of the cooling effectiveness. In an example where a cooled turbine engine component includes cooling holes, such estimates would need to account for the cooling effect of the gas moving through and out of the component.

Other techniques such as Tunable Diode Laser Absorption Spectroscopy (TDLAS) utilize a narrow diode laser at a specific wavelength and detect the absorption that certain gases have in the specific wavelength. In an environment where dust or other particulate matter may be present in the gas flow, one approach is to consider a passive system where locating an active laser or other optical sources in the particulate-containing environment is not required. For example, high temperatures around the combustor and exhaust can become prohibitive for locating a laser and cooling the laser to a set temperature in order to meet performance, power, or reliability needs.

The present disclosure incorporates the use of pyrometers, which can be used to measure the temperature of an uncooled component directly and non-intrusively at any combustion temperature regardless of the presence of particulate material in the gas flow, as well as optical sensors which provide the benefit of an improved temperature detection that can account for the cooling effect of exhausting gases through cooling holes in the component.

As discussed herein, the present disclosure includes a thermal measurement system with an optical sensor for sensing a wavelength indicative of an attenuation, the attenuation due to the optical sensor, and components thereof. The thermal measurement system provides a non-contact measurement of relatively high temperatures of a gas by sensing wavelengths of emitted light that pass through the gas from a surface of an object, including sampling wavelengths of light that are also partially or fully absorbed by the gas and reemitted based on the temperature of the gas and its relative emissivity. Attenuation, as is known, is associated with a gradual loss of flux intensity. The temperature sensing system herein can compensate for changes in attenuation of the overall sensor. Typically, an optical sensor can be composed of optical windows, lenses and other optical components. Since this optical sensor is located in a combustion environment, soot, carbon and other contaminates can coat optical components and changes their transmission characteristics. This change in transmission characteristics can affect the attenuation of the optical signal from the gas and blade emission that is received by optical detectors in the temperature sensing system.

The apparatus and method for determining a gas temperature described herein more accurately provides the gas temperature of gasses within an engine by accounting for attenuation. In an event where optical attenuation occurs and an emission of a gas for a particular temperature is known, uncertainty in determining the gas temperature can arise. This uncertainty arises because difficulty exists between discerning if a temperature change has actually occurred or if the sensed change arose from a change in attenuation. Therefore, as is described herein, deconvolving the optical attenuation is beneficial. Solutions for determining the optical attenuation include sensing wavelengths where the light emitted by the surface of the object is completely absorbed and re-emitted by at gas temperature closely matching black body emission, i.e. effective emissivity of the gas is equal to 1.

An optical sensor for sensing the wavelengths described herein can be provided in a pre-determined hole and permanently attached to the engine. Measurements of the exhaust gas in general are used to control the engine and also to perform prognostic health estimates to understand a lifespan of the engine. The thermal measurement system as described herein provides a fundamental measurement to run the engine. It is further contemplated that the optical sensor can be provided in existing borescope ports located within the turbine engine. Obtaining actual and accurate gas temperatures will aid in monitoring and validating of performance (e.g., blade/bucket performance) as well as aid in optimizing combustor performance. Both steady-state temperature data and transient temperature data can be obtained and used to track and measure local combustor performance and component health.

As used herein, the term "upstream" refers to a direction that is opposite the fluid flow direction, and the term "downstream" refers to a direction that is in the same direction as the fluid flow. The term "fore" or "forward" means in front of something and "aft" or "rearward" means behind something. For example, when used in terms of fluid flow, fore/forward can mean upstream and aft/rearward can mean downstream.

Additionally, as used herein, the terms "radial" or "radially" refer to a direction away from a common center. For example, in the overall context of a turbine engine, radial refers to a direction along a ray extending between a center longitudinal axis of the engine and an outer engine circumference. Furthermore, as used herein, the term "set" or a "set" of elements can be any number of elements, including only one.

All directional references (e.g., radial, axial, proximal, distal, upper, lower, upward, downward, left, right, lateral, front, back, top, bottom, above, below, vertical, horizontal, clockwise, counterclockwise, upstream, downstream, forward, aft, etc.) are only used for identification purposes to aid the reader's understanding of the present disclosure, and do not create limitations, particularly as to the position, orientation, or use of aspects of the disclosure described herein. Connection references (e.g., attached, coupled, connected, and joined) are to be construed broadly and can include intermediate members between a collection of elements and relative movement between elements unless otherwise indicated. As such, connection references do not necessarily infer that two elements are directly connected and in fixed relation to one another. The exemplary drawings are for purposes of illustration only and the dimensions, positions, order and relative sizes reflected in the drawings attached hereto can vary.

Turning to FIG. 1, a block diagram representation of a thermal measurement system (TMS) 10, in accordance with the disclosure herein is illustrated. The TMS 10 includes an object 12 emitting an emitted light 14. The emitted light 14 passes through a gas, or gasses, 16 towards the TMS 10. The TMS 10 can be utilized to measure a temperature of the gas 16, herein referred to as a gas temperature ($T_g$) and/or to measure a temperature of a surface of the object, herein referred to as an object temperature ($T_o$) in a variety of environments. By way of non-limiting example, the object 12 can be any stationary or moving object, or some combination thereof. For example, the object 12 can be any one, or more than one, hot gas path component of a gas turbine, such as the combustion liner, a turbine nozzle, a turbine stator, a turbine afterburner, and the like. Similarly, in the event the object is a moving object, it can be any traversing or rotating object typically located in a harsh environment, for example a turbine blade or a set of pistons. Aspects of the disclosure herein provide solutions and benefits for measuring temperatures in harsh environments (e.g., high temperatures), wherein the object temperature ($T_o$) can be in a range of between 500° F. and 3000° F. and/or the gas temperature ($T_g$) can be in a range of between 500° F. and 4000° F.

The TMS 10 described herein can be utilized to measure temperature of a variety of gases 16. In a typical combustion environment, the TMS 10 can be used where the gas 16 is, for example, carbon dioxide ($CO_2$), steam ($H_2O$), a hydrocarbon (e.g., natural gas, vaporized jet fuel, diesel gas, etc.), or some combination thereof. Other types of gases can be measured, as well by the TMS 10. Similarly, the TMS 10 can be utilized in a variety of pressurized environments, by way of non-limiting example, the pressure of the environment (e.g., combustion chamber) in which the gas 16 is present can be at 3 atmospheres or at least 5 atmospheres, and up to 6 atmospheres. The pressure can also dip as low as atmospheric pressure or a vacuum state.

The emitted light 14 passes through the gas 16 to define an infused light 18. Infused light 18 is defined as the total emitted light waves that travel from the object 12 and interact and are modified by the gas 16. An optical system 20 is spaced a measurable distance (L) from the object 12. The optical system 20 can include an optical sensor 22 which can include optical instruments 24, by way of non-limiting example an optical window 26, a lens 28, at least one filter 30, and at least one detector 32. The at least one filter 30 can be multiple filters for filtering the infused light 18 and the at least one detector 32 can be multiple detectors for measuring the infused light 18, therefore the filters 30 can be positioned prior to the detectors 32. It is contemplated, however, that the filters 30 and the detectors 32 are integral with each other, or that the filters 30 are integral with or part of other optical instruments 24 located prior to the detectors 32. The filters 30 can be band pass filters allowing light to pass through at specific wavelengths, either near infrared (NIR) wavelengths or long infrared (LIR) wavelengths. The detectors 32 can be, by way of non-limiting example photodiodes, such as an InGaAs that is either standard or extended range in its responsivity, GaP, Si, Ge, or a combination of Si/InGaAs. For sensed wavelengths beyond 2.6 μm, a thermopile is an option for the at least one detector 32. Other optical instruments 24, by way of non-limiting example at least one of a prism, a mirror, an optical fiber cable, and combinations thereof can be provided in the optical sensor 22 as well. The optical instruments 24 are configured within the optical sensor 22 to provide a current signal 34 between the optical sensor 22 and a translating device, by way of non-limiting example an amplifier 36. Assuming that the current signal 34 is large compared to any noise associated with a particular optical sensor 22, sensing NIR wavelengths will be more sensitive than sensing LIR wavelengths.

The amplifiers 36 can be configured to translate the current signal 34 into a transmitted signal 38, by non-limiting example to a voltage associated with a current and/or optical power from each of the detectors 32, for sending to a processor 40. It is contemplated that the detector and the amplifier together define an optical detector capable of converting light to current and then current to voltage with a single instrument. The processor 40 can include a computer processing unit (CPU) 42 for calculating the object temperature ($T_o$) and the gas temperature ($T_g$). By way of non-limiting example, the CPU 42 can be configured to process the transmitted signal 38 using an algorithm to provide the gas temperature ($T_g$). The processor 40 can further include a storage, by way of non-limiting example a look-up table 46, for storing a set of parameters 44, more specifically a set of spectroscopic parameters. The set of parameters 44 can be indicative of other required variables in determining the gas temperature ($T_g$).

The set of parameters 44 stored in the look-up table 46 can include, but is not limited to, various filter transmission (f) values associated with the installed filters 30, distances (L) related to the measurable distance between the optical sensor 22 and the object 12, various emissivity (ε) values associated with the object 12, various absorption factors (X) and/or pressure values (p). The look-up table 46 can further include ratio values, object temperatures (To), gas temperatures (Tg), and gas absorptions (A) associated with any given parameter or set of parameters. It should be understood that the filter transmission (f) and the distance (L) are known variables, the filter transmission (f) based on design and specification of the detector 32 and the wavelength selection, and the distance (L) based on a measurement between the optical sensor 22 and the object 12.

Sensors 48 can be placed in the surrounding environment of the TMS 10 or any other suitable location within the engine in which the TMS 10 is provided. A pressure sensor $48_p$ can sense the pressure (p) of the environment in which the object 12 and gas 16 are located. A gas absorption sensor 48x can sense an absorption factor (X) corresponding with a water concentration or a carbon dioxide concentration, or any other suitable gas concentration. The absorption factor (X) is a known behavior of a certain gas at a certain wavelength to absorb which is dependent on the gas mole fraction of the gas 16. A temperature sensor 48T can directly measure the object temperature ($T_o$).

In this manner, the TMS 10 is able to filter the infused light 18 and ultimately measure the gas temperature ($T_g$) and/or the object temperature ($T_o$). It should be noted that the disclosure herein is not limited to any particular processor for performing the processing tasks herein. The term "processor" is intended to denote any machine capable of performing the calculations, or computations, necessary to perform the tasks herein. The term "processor" is intended to denote any machine that is capable of accepting a structured input and of processing the input in accordance with prescribed rules to produce an output. It should also be noted that the phrase "configured to" as used herein means that the processor is equipped with a combination of hardware and software for performing the tasks herein, as will be understood by those skilled in the art.

Figure 2:
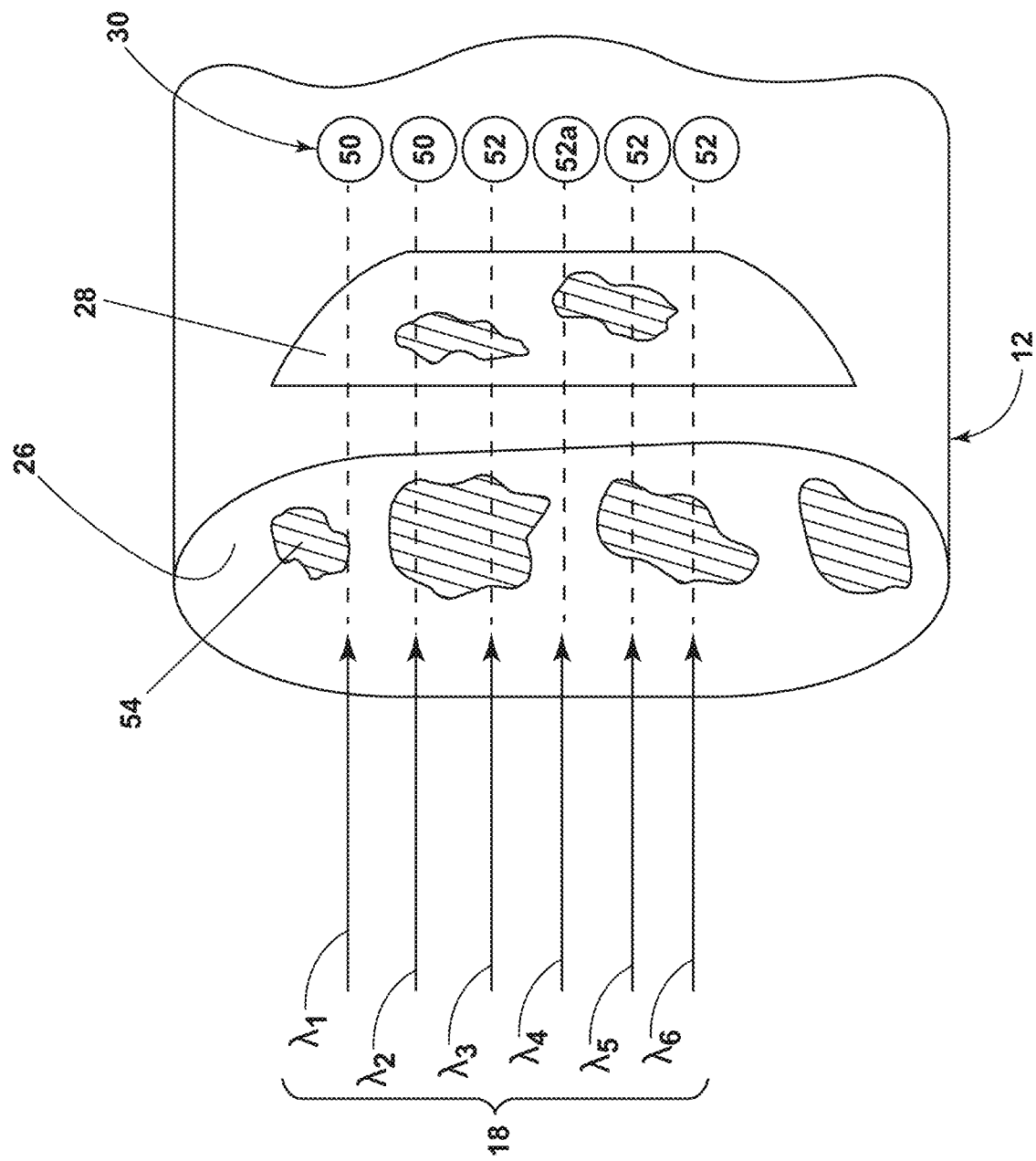
FIG. 2 is an enlarged view of a portion of the thermal measurement system including the optical sensor from FIG. 1.

Turning to FIG. 2, is an enlarged schematic of the optical system 20 illustrating six filters 30 each for differentiating specific wavelengths ($\lambda_1, \lambda_2, \lambda_3, \lambda_4, \lambda_5, \lambda_6$) from the infused light 18. While six filters are illustrated more or less filters 30 are contemplated. One or more filters 30 can be selected with a particular detection wavelength ($\lambda_1, \lambda_2$) or wavelength range, that corresponds to light emitted directly from the object 12 where gas minimally absorbs/emits the light 14, herein these filters 30 will be referred to simply as object filters 50. Each of the object filters 50 is set up to collect a first and second wavelength ($\lambda_1, \lambda_2$) is associated in particular with the object temperature ($T_o$).

Similarly, one or more filters 30 can be selected with a particular detection wavelength, a third, fourth, fifth, and sixth wavelength ($\lambda_3, \lambda_4, \lambda_5, \lambda_6$) or wavelength range, that corresponds to where the gas 16 substantially absorbs/emits the light 14, herein these filters will be referred to simply as gas filters 52. At least one of the gas filters 52 can be associated specifically with attenuation, referred to herein as an attenuation filter 52a. It is contemplated that any one of the gas filters 52 can be utilized as an attenuation filter 52a. As previously mentioned herein, the attenuation is due to environmental factors, by way of non-limiting example contaminates 54 that can coat the optical instruments and change their transmission characteristics. A wavelength independent fouling factor (F) can be determined by the processor using the wavelength ($\lambda_4$) signature associated with the attenuation filter 52a. Each of the other filters 30 set up to collect third, fifth, and sixth wavelengths ($\lambda_3, \lambda_5, \lambda_6$) can be associated in particular with variables including, but not limited to, gas absorption factor (X), pressure (p), gas temperature ($T_g$), and attenuation. A method for determining the fouling factor (F) that represents attenuation affecting all filters 30 equally, will be described in more detail herein.

Figure 3:
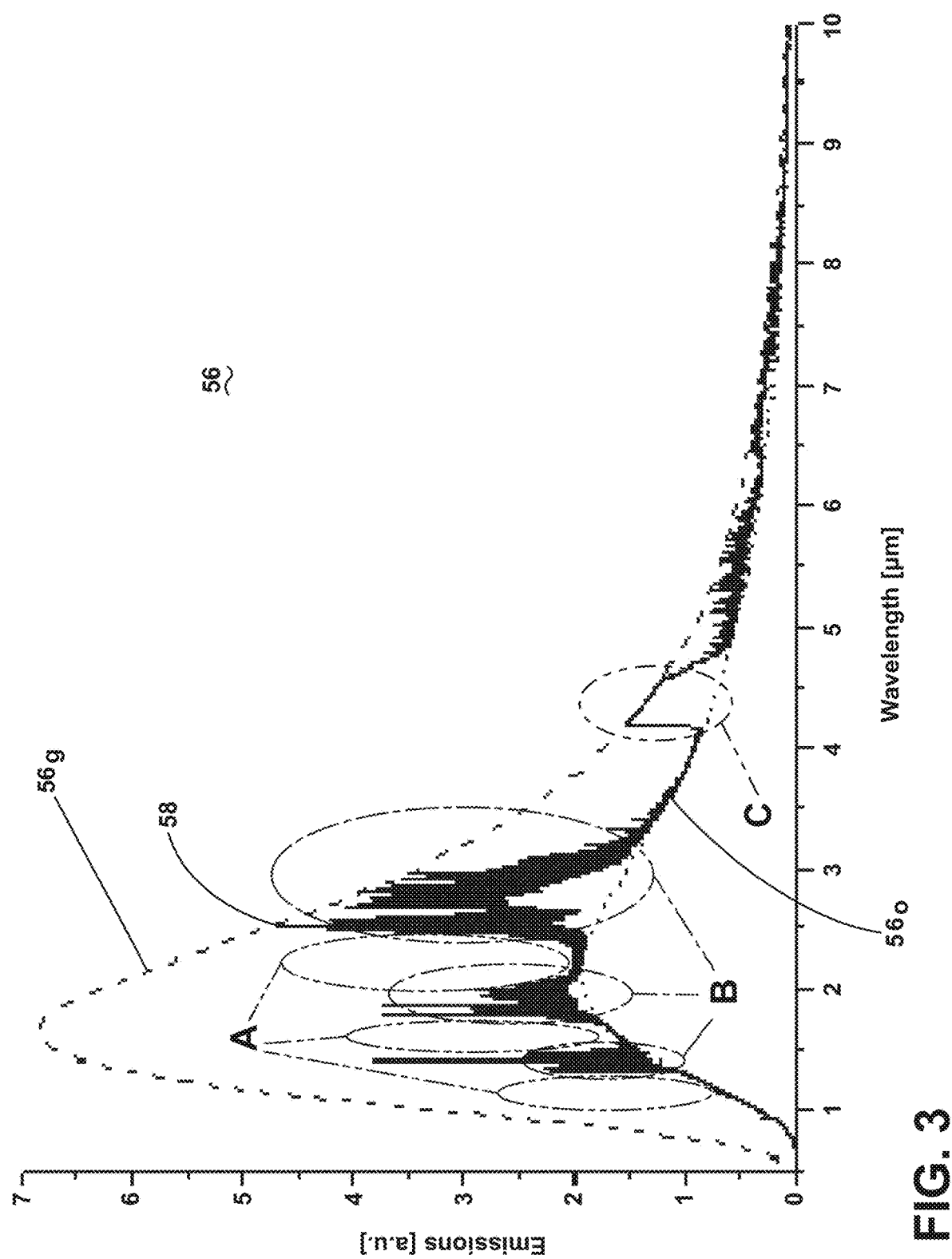
FIG. 3 is an emissivity graph depicting an exemplary emission/absorption for light emitted from the object of FIG. 1.

FIG. 3 illustrates a curve 56 depicting emission of light as compared to wavelength for light as it passes from an object, by way of non-limiting example the object 12, through a gas, by way of non-limiting example the gas 16. The emission of an object or a gas is governed by Plank's law which this is an illustration of at two different temperatures. The object 12 is at a lower temperature, illustrated by the smaller curve 56o, than the gas 16, illustrated by the larger curve 56g. The curve 56 represents $H_2O$ behavior at a certain pressure (p) and gas absorption factor (X) and distance (L), other gases or even $H_2O$ at different certain pressure (p) and gas absorption factors (X) would look different. It should be understood, however, that the $H_2O$ will still have the same regions of transmission and absorption, only the magnitude of the gas interaction changes. Aspects of the disclosure herein utilize information on the curve 56. As the curve 56 shows, light at certain wavelengths, or intensities, passes through the gas 16 with minimum, or little to no absorption/emission by the gas 16. Some of the minimum absorption/emission regions are depicted by circled regions "A". Similarly, light at certain wavelengths, or intensities, passes through the gas 16 and is substantially, or highly absorbed/emitted by the gas 16 depicted by gas absorption peaks 58. This is due to the higher temperature of the gas and the absorption and subsequent re emission of the light from this higher temperature gas. Some of the substantial regions are depicted by circled regions "B". Additionally, circled region "C" includes wavelengths from about 4 μm to about 5 μm, where gas 16 absorbs and re-emits light to closely match a black body emission at the gas temperature, wherein an effective emissivity of the gas is equal to 1. While wavelengths in regions "A" and "B" are affected by both the object 12 and the gas 16, wavelengths measured in region "C" are unaffected by the solid object. The wavelength signal 34 changes with temperature via the Planck equation, the ideal gas equation, and the temperature dependence of the gas absorption peaks 58.

Figure 4:
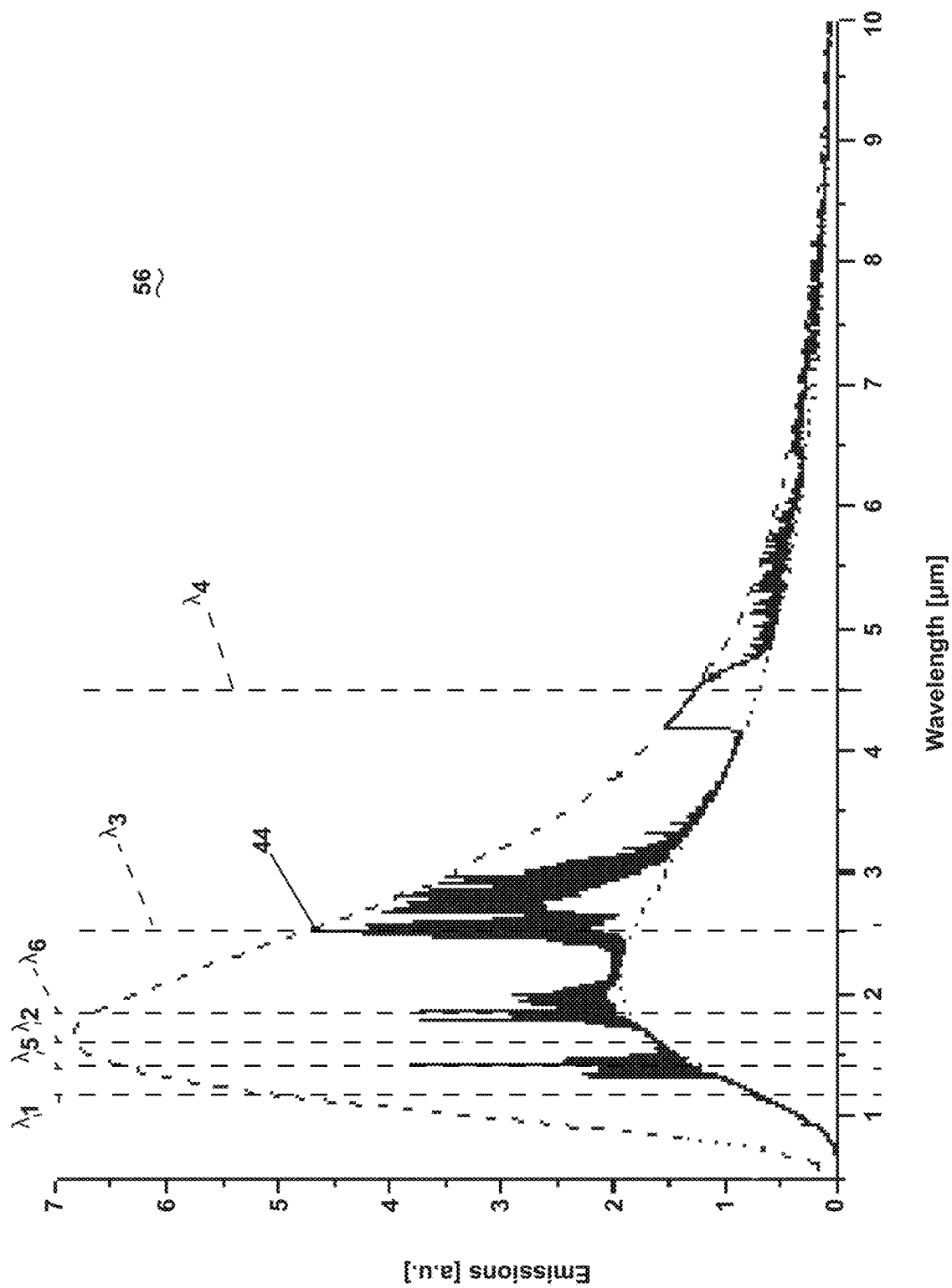
FIG. 4 is the emissivity graph of FIG. 3 illustrating specific wavelengths.

FIG. 4 illustrates the curve 56 again where circled regions A, B, and C have been removed for clarity. As previously discussed, the TMS 10 processes information from light collected that was originally emitted from the surface of object 12. These wavelengths range from between 0.5 μm and 10 μm. Depending on the particular gas, or gasses, 16, the filters 30 used in the TMS 10 that have detection ranges that align with at least one of the circled regions "A" (FIG. 2), at least one of the circled regions "B" (FIG. 2), and at least one of the circled regions "C" (FIG. 2). Two vertical dashed lines along first and second wavelengths ($\lambda_1, \lambda_2$) correspond with object filters 50 that can be used to detect light minimally absorbed/emitted by the particular gas 16. The first wavelength ($\lambda_1$) can be between 1200 and 1300 nm, by way of non-limiting example the first wavelength ($\lambda_1$) can be equal to 1240 nm. The second wavelength ($\lambda_2$) can be between 1550 and 1700 nm, by way of non-limiting example the second wavelength ($\lambda_1$) can be equal to 1625 nm. Four vertical dashed lines along third, fourth, fifth, and sixth wavelengths ($\lambda_3, \lambda_4, \lambda_5, \lambda_6$) correspond with the gas filters 52 that can be used to detect light substantially absorbed/emitted by the particular gas 16.

The vertical dashed line along the fourth wavelength ($\lambda_4$) in particular can correspond with the attenuation filter 52a. The fourth wavelength ($\lambda_4$), or attenuation wavelength, can correspond to a wavelength range between 4100 and 4700 nm, by way of non-limiting example the attenuation wavelength ($\lambda_4$) can be equal to 4500 nm. An exemplary attenuation filter 52a can be set up to detect light that closely matches the gas emission, wherein all of the light emitted by the object 12 is absorbed by the gas 16 and emitted by the gas at the gas temperature ($T_g$) with an effective emissivity of 1.

The six wavelengths ($\lambda_1, \lambda_2, \lambda_3, \lambda_4, \lambda_5, \lambda_6$) described herein can be central wavelengths associated with each of the filters 30. By way of non-limiting example when the filters 30 are bandpass filters as described herein, the filter 30 has a bandpass width that can be 2-100 nm wide depending on the filter 30. Therefore each filter 30 can have a center wavelength and a wavelength range. In this example, wide widths are associated with more signal and narrow widths are associated with higher sensitivity.

Figure 5:
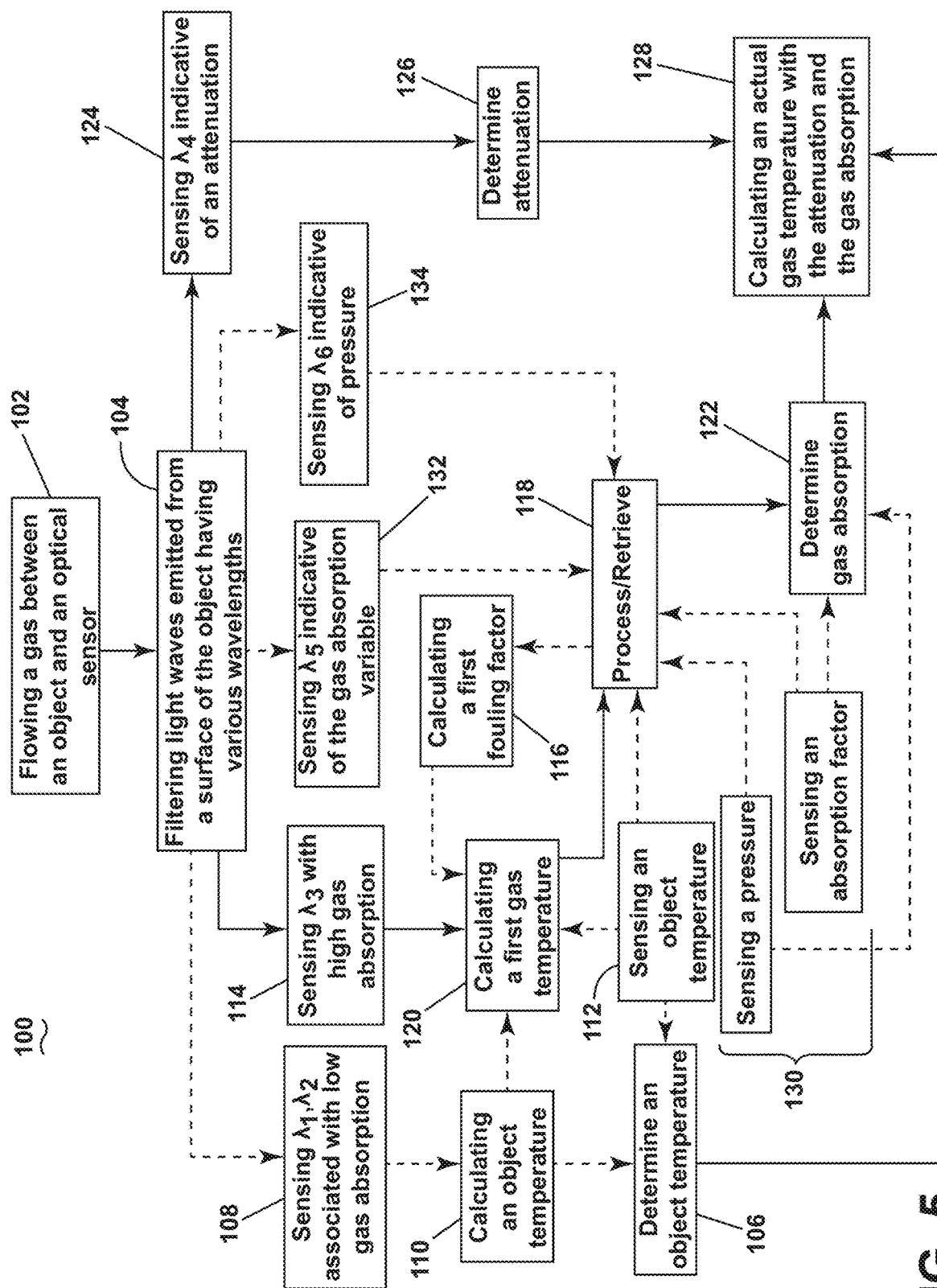
FIG. 5 is a flow chart depicting a method of measuring a temperature of gas using the thermal management system of FIG. 1.

Turning to FIG. 5, a method 100 of determining the temperature of the gas ($T_g$) is illustrated in a flow chart. At 102, the gas 16 flows between the object 12 and the optical sensor 22. At 104, emitted light waves 14, having passed through the gas 16 to define infused light 18, are filtered. The object temperature is determined at 106. In one exemplary determination, the object filters 50 can be configured to sense the first and second wavelengths ($\lambda_1, \lambda_2$) at 108, each associated with a low gas absorption, for determining the object temperature ($T_o$) using a first equation:

$$I_{1,2} = F \times f_{1,2} \times \varepsilon \times P(\lambda_{1,2}, T_o)$$

The first equation is a function of the wavelength independent fouling factor (F) associated with attenuation, a filter transmission (f), an emissivity (ε) of the object, the filtered wavelength, either the first or second ($\lambda_1$) or ($\lambda_2$), and the object temperature ($T_o$). $P(\lambda_{1,2}, T_o)$ simply represents implementing Planck's Law. The wavelength independent fouling factor (F), the emissivity (ε), and the object temperature ($T_o$) are all the same for either $I_1$ or $I_2$, and the filter transmission (f) is known for both filters 30, therefore, with two equations and two unknowns ($T_o$, (F×ε)), the equations can be utilized to calculate the object temperature ($T_o$) at 110. It is further contemplated that the object temperature ($T_o$) is determined by alternate techniques including by sensing the object temperature ($T_o$) at 112 with the sensor 48$_T$ capable of directly measuring the object temperature ($T_o$).

The gas filters 52 can be configured to sense the third wavelength ($\lambda_3$) at 114, associated with a high gas absorption, for determining gas temperature ($T_g$) using a second equation:

$$I_3=F \times f_3 \times \{\varepsilon \times P(\lambda_3,T_o) \times A + P(\lambda_3,T_g) \times (1-A)\}$$

Utilizing the calculated or sensed object temperature ($T_o$), the product (F×ε) of the fouling factor (F) and the emissivity (ε) of the object can now be determined, however neither the fouling factor (F) or the emissivity (ε) individually are known. The second equation is a function of the wavelength independent fouling factor (F), a filter factor (f) associated with the gas filter 52, the object emissivity (s), the third wavelength (h), the object temperature ($T_o$), the gas temperature ($T_g$), and a gas absorption (A). The gas absorption (A) is a function of the third wavelength (h), the gas temperature ($T_g$), the distance (L), the absorption factor (X), and the pressure (p). A ratio between the first equation ($I_{1,2}$) related to either one of the first wavelength ($\lambda_1$) or the second wavelength ($\lambda_2$), and the second equation ($I_3$) can be utilized to calculate the first gas temperature ($T_g'$). With two equations and three unknowns (F, A, and $T_g$) there are multiple iterations that can be conducted. Either an attenuation in terms of a fouling factor (F) needs to be determined or a gas absorption (A) needs to be determined in order to calculate the gas temperature ($T_g$).

Utilizing the calculated value of (F×ε) an estimate of the attenuation can be determined by calculating a first fouling factor (F') at 116 by utilizing an emissivity (ε) value based on the material used for the object 12 that is retrieved from, at 118, by way of non-limiting example, the look-up table 46. This approximate emissivity (s') based on the material can change as the engine is operated, however it is a reasonable value to calculate the first fouling factor (F'). With the first fouling factor (F'), and two equations and two unknowns (A, Tg), the first gas temperature ($T_g'$) can now be calculated at 120. The gas temperature ($T_g$) at this point is only an approximation as it has been found that when using the ratio method ($I_3/I_1$), the error is about −20K at a gas temperature of 1500K (~2200 F) and increases to −50K at $T_g$=1800K (~2700 F). Even ignoring the uncertainty of the first fouling factor (F'), the use of $I_3$ directly creates a large error in gas temperature ($T_g$) unless the temperature of the object ($T_o$) is very small. It should be understood that the gas absorption (A) can now be determined at 122 utilizing the first fouling factor (F'), though it should be understood that because the gas absorption (A) is also dependent on the gas temperature ($T_g$), the solution is non-linear in that it can be processed repeatedly at 118.

In order to account for attenuation, at 124 the attenuation wavelength ($\lambda_4$) can be sensed and can be utilized to determine the attenuation at 126 by finding the actual fouling factor (F). In region "C" where the gas absorption (A) is very high compared to the distance (L) from the object 12 emitting the wavelengths to the optical sensor 22, the wavelength signal 34 becomes independent of the object temperature ($T_o$) and the gas absorption (A). The second equation therefore simplifies to:

$$I_4=F \times f_4 \times P(\lambda_4,T_g)$$

Utilizing the simplified second equation with attenuation wavelength ($\lambda_4$), the actual fouling factor (F) can be determined without the gas absorption (A), and more specifically either of the absorption factor (X) or pressure (p). A ratio of ($I_4/I_1$) can be utilized with two equations and two unknowns (F, $T_g$) to calculate the fouling factor (F). It is further contemplated that the irradiance ($I_4$) can be directly calculated by measuring the flux and utilizing the attenuation wavelength ($\lambda_4$). Utilizing the equations and calculated values described herein, an algorithm executed by the processor 40 can then more accurately calculate a corrected gas temperature ($T_g$) at 128.

The gas absorption (A) determined at 122 can also be utilized in the algorithm. The gas absorption (A) is dependent on the wavelength ($\lambda$) value, the absorption factor value (X), the pressure (p) and the gas temperature ($T_g$). It is contemplated that the absorption factor (X) and/or the pressure (p) can be directly determined with sensors 48X, 48p using real-time measurements at 130. It is further contemplated that one of the absorption factor (X) or the pressure (p) be retrieved from the look-up table 46 118 utilizing the other of the absorption factor (X) or pressure (p), whichever one was sensed in real-time, and any other calculated or known variables. Other calculated or known variables necessary for retrieving the absorption factor (X) or the pressure (p) from the look-up table include the ratio values calculated herein, the first gas temperature ($T_g'$) and the object temperature ($T_o$). An algorithm can be applied to retrieve either one of the absorption factor (X) and/or pressure (p) values needed. While the absorption factor (X) and/or pressure (p) determined here is based on the first gas temperature ($T_g'$), in a scenario where the method has been implemented over multiple iterations, the first gas temperature (Tg') is becoming closer to the actual gas temperature ($T_g$) over time, and in some iterations is equal to the actual gas temperature ($T_g$). Utilizing the attenuation sensor 52a increases the accuracy and decreases the iteration requirements.

It is further contemplated that fifth and sixth detectors 30 are utilized to filter the fifth and sixth wavelength ($\lambda_5$, $\lambda_6$). At 132 the fifth wavelength ($\lambda_5$) can be filtered and sensed by the optical sensor 22. A table associated with the fifth wavelength ($\lambda_5$) and the corresponding second equation ($I_5$), along with the other parameters described herein can be stored in the look-up table 46. At 134 the sixth wavelength ($\lambda_6$) can be filtered and sensed by the optical sensor 22. Another table associated with the sixth wavelength ($\lambda_6$) and the corresponding second equation ($I_6$), along with the other parameters described herein can be stored in the look-up table 46. Ratios ($I_5/I_1$) and ($I_6/I_1$) between the first equation and the second equation each create three unknowns (F, A, and $T_g$). Utilizing the ratio ($I_3/I_1$) an algorithm can be applied to find $T_g$, X, and p that satisfy all three ratios ($I_3/I_1$, and $I_6/I_1$) and pull from the table the unknown variable either the absorption factor (X) or the pressure (p).

It should be understood that the method as described herein can occur in multiple sequences to achieve the accurate temperature values. Multiple iterations of the method herein enable a tracking of the emissivity (ε) and fouling factor (F) changes over time. While many of the factors can change during operation, typically the emissivity (ε) and fouling factor (F) change slowly over time. These values can also be used to feed iterations of the subsequent calculations. Factoring in these slower changes allows for more accurate real-time data. Furthermore, if the emissivity (ε) and/or fouling factor (F) change drastically during a relatively short period of time, detecting these changes can improve maintenance engine function.

Figure 6:
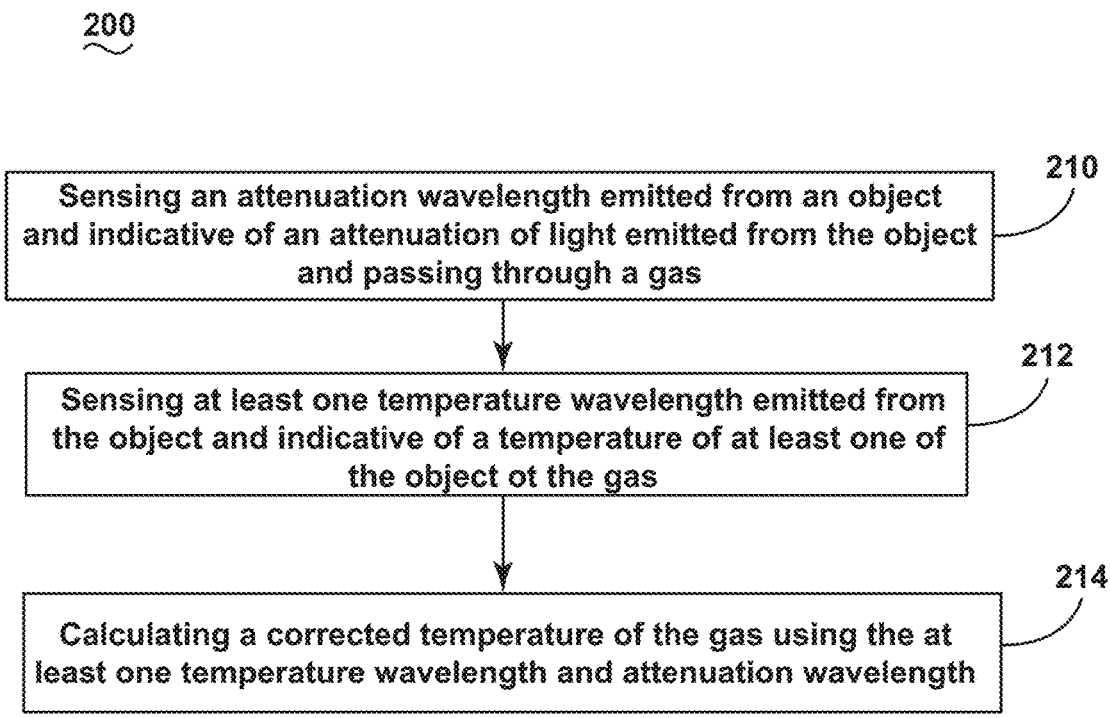
FIG. 6 is a flow chart depicting another method of measuring a temperature of gas using the thermal management system of FIG. 1.

Turning to FIG. 6, a flow chart depicting a method 200 of determining a temperature of the gas 16 in a system with the object 12, the optical sensor 22, and the gas 16 passing between the object 12 and the optical sensor 22. At 210 the optical sensor 22 is configured to sense the attenuation wavelength, referred to herein as the fourth wavelength ($\lambda_4$), where the attenuation wavelength is emitted from the object 12 and indicative of the attenuation, by way of non-limiting example the fouling factor (F) described herein. At 212 the optical sensor 22 is configured to sense at least one temperature wavelength, herein the first, second, and third wavelengths ($\lambda_1$, $\lambda_2$, $\lambda_3$), emitted from the object 12 and indicative of the object temperature ($T_o$) or the first gas temperature ($T_g'$). At 214, the method includes calculating, by way of non-limiting example with the CPU 42, a corrected gas temperature ($T_g$) of the at least one of the gas 16 using the at least one temperature wavelength ($\lambda_1$, $\lambda_2$, $\lambda_3$) and the attenuation wavelength ($\lambda_4$).

Benefits associated with the apparatus and method described herein include maintenance of temperature measurement accuracy. During engine operation, the object emissivity will change on any given part due to aging or buildup of material. This changes the readings of the system at a particular operating condition. The emissivity of either the object, scales the signal level received by the detector. The attenuation has a similar effect on the signal, in that as there is buildup on the optical components or any source of change in the signal level (degradation of optical components), a reduction of the signal level across all the wavelengths of interest for both light originating from the object and light from the gas will occur. The use of the method described herein allows for the system account for changes in the signal level over the life of the system and whether they originate from changes in emissivity or changes in attenuation. Accounting for this information improves the accuracy of the measurement because attenuation affects all the light through the optical system while object emissivity only affects the light originating from the object and doesn't affect the gas emission.

It should be appreciated that application of the disclosed design is not limited to turbine engines with fan and booster sections, but is applicable to turbojets and turboprop engines as well.

This written description uses examples to describe aspects of the disclosure described herein, including the best mode, and also to enable any person skilled in the art to practice aspects of the disclosure, including making and using any devices or systems and performing any incorporated methods. The patentable scope of aspects of the disclosure is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims.

Various characteristics, aspects, and advantages of the present disclosure can also be embodied in the following technical solutions as defined by the clauses:

A method of determining a temperature in a system having an object, an optical sensor, and a gas flow passing between the object and the optical sensor, the method comprising sensing, with the optical sensor, an attenuation wavelength emitted from the object and indicative of an attenuation associated with the optical sensor; sensing, with the optical sensor, at least one temperature wavelength emitted from the object and indicative of a temperature of at least one of the object or the gas; and calculating a temperature of the gas using the at least one temperature wavelength and the attenuation wavelength.

The method of any preceding clause, wherein sensing the attenuation wavelength comprises sensing a wavelength where the gas absorbs and re-emits light to closely match a black body emission having an effective emissivity equal to 1.

The method of any preceding clause, wherein sensing the attenuation wavelength comprises sensing a wavelength of between 4100 and 4700 nm.

The method of any preceding clause, further comprising sensing at least one wavelength associated with a high gas absorption.

The method of any preceding clause, wherein sensing the at least one temperature wavelength comprises sensing a first wavelength of between 1200 nm and 1300 nm and sensing a second wavelength of between 1550 nm and 1700 nm.

The method of any preceding clause, further comprising sensing with the optical sensor a gas absorption wavelength indicative of a gas absorption factor of the gas.

The method of any preceding clause, further comprising sensing with the optical sensor a pressure wavelength indicative of a pressure of the gas.

A method of determining a temperature of a gas, the method comprising flowing a gas between an object and a thermal measurement system, the thermal measurement system comprising at least an optical sensor and a processor; filtering, with the optical sensor, light waves emitted from a surface of the object and having various wavelengths; sensing, with the optical sensor a gas wavelength associated with a high gas absorption and an attenuation wavelength indicative of an attenuation of the optical sensor; calculating, with the processor, a first gas temperature using the gas wavelength; determining a temperature of the object; retrieving, from a database provided in the processor, at least one parameter indicative of a gas absorption and associated with the object temperature and the first gas temperature; determining the gas absorption; calculating, with the processor, the attenuation of the optical sensor using the attenuation wavelength; and calculating an actual gas temperature with the attenuation and the gas absorption.

The method of any preceding clause, wherein determining the temperature of the object comprises one of directly sensing the temperature of the object with a sensor or sensing with the optical sensor a first wavelength and a second wavelength different from the first wavelength, each associated with a low gas absorption and calculating, with the processor, an object temperature using the first wavelength and the second wavelength.

The method of any preceding clause, wherein sensing the first wavelength comprises sensing a wavelength of between 1200 nm and 1300 nm.

The method of any preceding clause, wherein sensing the second wavelength comprises sensing a wavelength of between 1550 nm and 1700 nm.

The method of any preceding clause, wherein sensing the attenuation wavelength comprises sensing a wavelength where the gas emits and absorbs light to closely match a black body emission having an effective emissivity equal to 1.

The method of any preceding clause, wherein sensing the attenuation wavelength comprises sensing a wavelength of between 4100 and 4700 nm.

The method of any preceding clause, further comprising sensing at least one of a gas absorption factor or a pressure associated with the gas.

The method of any preceding clause, further comprising sensing with the optical sensor an additional wavelength associated with the other of the gas absorption factor or the pressure associated with the gas.

A thermal measurement system for determining the temperature of a gas disposed around an object, the thermal measurement system comprising an optical sensor spaced from the object a predetermined distance, the optical sensor comprising an attenuation filter associated with an attenuation of wavelengths reaching the object having passed through the gas; an optical detector for translating the attenuation wavelength signal into a transmitted signal; and a processor configured to receive the transmitted signal, the processor comprising a storage for storing a set of parameters and a computer for determining at least one parameter from the set of parameters associated with the transmitted signal and calculating a gas temperature of the gas utilizing the transmitted signal and the at least one parameter.

The thermal measurement system of any preceding clause, wherein the optical sensor further comprises at least one object temperature filter associated with a temperature of the object.

The thermal measurement system of any preceding clause, wherein the optical sensor further comprises at least one gas temperature filter associated with a temperature of the gas.

The thermal measurement system of any preceding clause, further comprising at least one of a pressure sensor for sensing a pressure variable or a gas absorption sensor for sensing a gas absorption.

The thermal measurement system of any preceding clause, further comprising at least one additional filter for capturing an additional wavelength associated with the other the pressure variable or the gas absorption.

What is claimed is:

1. A thermal measurement system for determining a temperature of a gas disposed around an object, the thermal measurement system comprising:
    an optical sensor spaced from the object a predetermined distance, the optical sensor comprising an attenuation filter associated with an attenuation of the optical sensor determined by an attenuation wavelength reaching the optical sensor from the object after having passed through the gas;
    an optical detector for translating a wavelength signal, including the attenuation wavelength, into a transmitted signal;
    a storage for storing a set of parameters, including at least an emissivity value associated with the object; and
    a processor configured to:
        receive the transmitted signal,
        determine at least one parameter associated with the transmitted signal from the set of parameters,
        determine a fouling factor based on the attenuation wavelength, and
        calculate a gas temperature of the gas utilizing at least the fouling factor and the at least one parameter.

2. The thermal measurement system of claim 1, wherein the optical sensor further comprises at least one object temperature filter associated with a temperature of the object.

3. The thermal measurement system of claim 1, wherein the optical sensor further comprises at least one gas temperature filter associated with a temperature of the gas.

4. The thermal measurement system of claim 1, further comprising at least one of a pressure sensor for sensing a pressure variable or a gas absorption sensor for sensing a gas absorption wherein either the pressure variable or the gas absorption are part of the set of parameters.

5. The thermal measurement system of claim 4, further comprising at least one additional filter for capturing an additional wavelength associated with the other of the pressure variable or the gas absorption.

6. A method of determining a temperature with the thermal measurement system of claim 1, the method comprising:
    sensing, with the optical sensor, an attenuation wavelength emitted from the object and indicative of an attenuation associated with the optical sensor;
    sensing, with the optical sensor, at least one temperature wavelength emitted from the object and indicative of a temperature of at least one of the object or the gas; and
    calculating, with the processor, a temperature of the gas using the at least one temperature wavelength and the attenuation wavelength.

7. The method of claim 6, wherein sensing the attenuation wavelength comprises sensing a wavelength where the gas absorbs and re-emits light to closely match a black body emission having an effective emissivity equal to 1.

8. The method of claim 6, wherein sensing the attenuation wavelength comprises sensing a wavelength of between 4100 and 4700 nm.

9. The method of claim 6, wherein sensing the at least one temperature wavelength comprises sensing a first wavelength of between 1200 nm and 1300 nm and sensing a second wavelength of between 1550 nm and 1700 nm.

10. A method of determining a temperature of a gas using the thermal measurement system of claim 1, the method comprising:
    flowing the gas between the object and the thermal measurement system;
    filtering, with the optical sensor, light waves emitted from a surface of the object and having various wavelengths;
    sensing, with the optical sensor, a gas wavelength, wherein the gas wavelength is associated with a high gas absorption and an attenuation wavelength indicative of an attenuation of the optical sensor;
    calculating, with the processor, a first gas temperature using the gas wavelength;
    determining, with the processor, a temperature of the object;
    retrieving, from a database via the processor, at least one parameter indicative of a gas absorption and associated with the temperature of the object and the first gas temperature;
    determining, with the processor, the gas absorption based on the at least one parameter;
    calculating, with the processor, the attenuation of the optical sensor using the attenuation wavelength; and
    calculating, with the processor, an actual gas temperature with the attenuation and the gas absorption.

11. The method of claim 10, wherein sensing the attenuation wavelength comprises sensing a wavelength where the gas emits and absorbs light to closely match a black body emission having an effective emissivity equal to 1.

12. The method of claim 10, wherein sensing the attenuation wavelength comprises sensing a wavelength of between 4100 and 4700 nm.

13. The method of claim 10, further comprising sensing, with the optical sensor, an additional wavelength associated with the other of a gas absorption factor or a pressure wavelength indicative of a pressure of the gas to calculate, with the processor, the actual gas temperature.

14. The method of claim 10, wherein determining the temperature of the object comprises one of directly sensing the temperature of the object, with a sensor, or sensing with the optical sensor a first wavelength and a second wavelength different from the first wavelength, each associated with a low gas absorption and calculating, with the processor, the object temperature using the first wavelength and the second wavelength.

15. The method of claim 14, wherein sensing the first wavelength comprises sensing a wavelength of between 1200 nm and 1300 nm.

16. The method of claim 15, wherein sensing the second wavelength comprises sensing a wavelength of between 1550 nm and 1700 nm.

\* \* \* \* \*